United States Patent [19]

Jingu

[11] Patent Number: 4,491,137
[45] Date of Patent: Jan. 1, 1985

[54] ADAPTOR FOR ULTRASONIC TRANSDUCER PROBE

[75] Inventor: Masaharu Jingu, Ootawara, Japan

[73] Assignee: Tokyo Shibaura Denki Kabushiki Kaisha, Kawasaki, Japan

[21] Appl. No.: 521,825

[22] Filed: Aug. 10, 1983

[30] Foreign Application Priority Data

Aug. 17, 1982 [JP] Japan .................. 57-124405[U]

[51] Int. Cl.³ .............................................. A61B 10/00
[52] U.S. Cl. ................................................... 128/660
[58] Field of Search ............. 128/660, 661, 663, 24 A

[56] References Cited

U.S. PATENT DOCUMENTS 4,408,611 10/1983 Enjoji .................................. 128/660

OTHER PUBLICATIONS

Taylor, W. B. et al., "A High-Resolution Trans-Rectal UTS System", UTS in Medicine & Biology, pp. 129–138, Pergamon Press 1979.

*Primary Examiner*—Kyle L. Howell
*Assistant Examiner*—Francis J. Jaworski
*Attorney, Agent, or Firm*—Cushman, Darby & Cushman

[57] ABSTRACT

An adaptor for a cannula guide type ultrasonic transducer probe which guides a cannula along a cavity of the ultrasonic transducer probe and which holds a bag covering said probe in position which comprise a guide unit having a substantially trapezoidal back plate and a pair of side plates, said back plate having a shape complementary to the shape of a back wall of said cavity, and said pair of side plates being integrally formed with said back plate along two sides thereof; and a band unit mounted such that upper and lower free ends thereof respectively extend from upper and lower ends of said back plate, said upper and lower free ends of said band unit having engaging means, respectively.

9 Claims, 8 Drawing Figures

ADAPTOR FOR ULTRASONIC TRANSDUCER PROBE

BACKGROUND OF THE INVENTION

1. Field of the Invention

The present invention relates to an adaptor for a cannula guide type ultrasonic transducer probe for securing a disinfection cover on the ultrasonic transducer probe so as to prevent the probe from being contaminated.

2. Description of the Prior Art

In order to remove body tissue or body fluid from organs such as a liver or kidney by means of a cannula for diagnosis, a cannula guide type ultrasonic transducer probe (to be referred to as a probe hereinafter) is conventionally used to monitor the movement of the cannula inserted in an examination object such as a liver, thereby guaranteeing safety during the examination. A probe of this type is described in U.S. Pat. No. 4,289,139 wherein safety and ease of disinfection/sterilization are well considered. This probe comprises: a carrier having a plurality of ultrasonic transducer elements and a cannula guide cavity; and a cannula guide block having a shape which fits in the cavity and a including cannula guide slot. The ultrasonic transducer elements are aligned in a row and can be brought into contact with a body surface portion. Contamination of this probe through the cannula is, as far as possible, prevented by the guide block.

Though having such a contamination-proof construction, the probe may be contaminated by blood from a patient at the time of cannulation and by blood in the cannula (i.e., cellular fluids and blood attached to the distal end of the cannula) at the time of removal. This contamination could cause serum hepatitis B. In order to avoid this, the probe must be sufficiently disinfected and sterilized every time it is used. However, along with an increase in patients who must be given the ultrasonic examination described above, a sufficient number of patients cannot be examined if the probe is disinfected and sterilized every time it is used.

SUMMARY OF THE INVENTION

The present invention has been made in consideration of the above situation and has for its object to provide an adaptor for a cannula guide type ultrasonic transducer probe to prevent contamination of the probe when used together with a cannula, thereby eliminating a disinfection procedure of the probe every time the probe is used.

In order to achieve the above object, there is provided an adaptor for a cannula guide type ultrasonic transducer probe which guides a cannula along a cavity of the ultrasonic transducer probe and which holds a bag covering said probe in position, said cavity being formed in one major surface of said probe and being tapered along an array of ultrasonic transducer elements so as to become wider in a direction from an application surface which has the ultrasonic transducer elements thereon to an opposite surface thereto, comprising: a guide unit having a substantially trapezoidal back plate and a pair of side plates, said back plate having a shape complementary to a shape of a back wall of said cavity and fitted in said cavity through said bag, and said pair of side plates being integrally formed with said back plate along two sides thereof; and a band unit with upper and lower free ends respectively extending from upper and lower ends of said back plate, said upper and lower free ends of said band unit having engaging means, respectively.

DETAILED DESCRIPTION OF THE PREFERRED EMBODIMENTS

Figure 1:
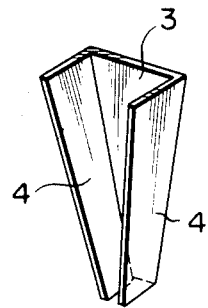
FIG. 1 is a perspective view of the main part of an adaptor for an ultrasonic transducer probe according to a first embodiment of the present invention.

FIG. 1 shows the main part (guide unit) of an adaptor for an ultrasonic transducer probe according to a first embodiment of the present invention. The guide unit comprises: a substantially V-shaped back plate 3 complementary to the shape of the back wall of a wedge-shaped cavity 2 (FIG. 3) formed in the front side of an ultrasonic transducer probe 1 (FIG. 3); and a pair of side walls 4 integrally formed with the back plate 3 along two sides thereof. The adaptor main part preferably comprises a hard material such as metal or a rigid plastic.

Figure 2:
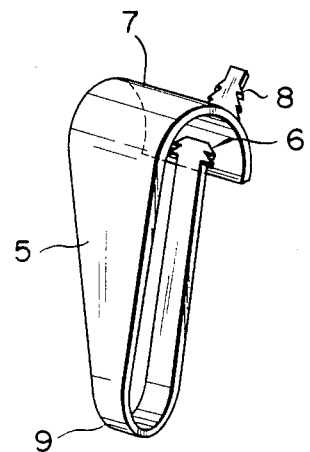
FIG. 2 is a perspective view of the band unit of the adapter shown in FIG. 1.
Figure 3:
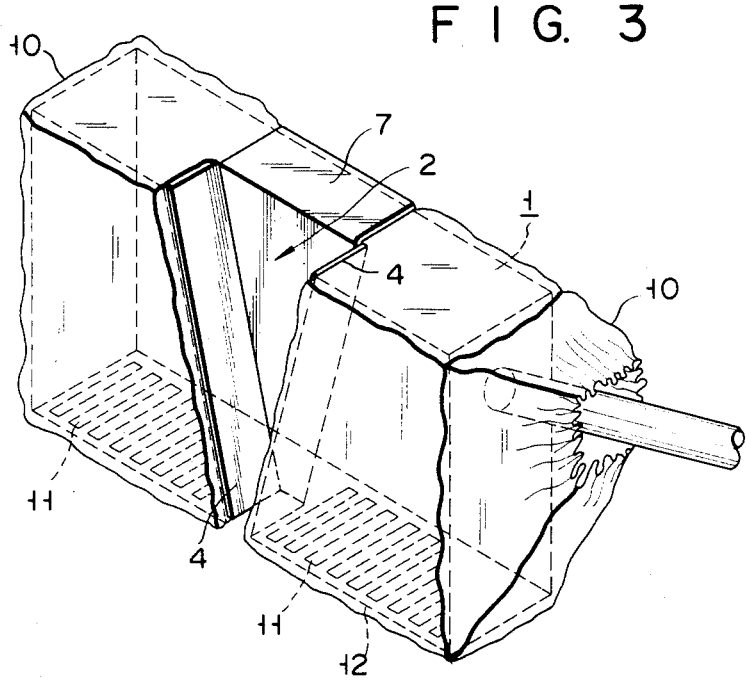
FIG. 3 is a perspective view of the adaptor, illustrating how the adaptor is used.

FIG. 2 shows a band unit for mounting the guide unit in the cavity 2 in a manner as shown in FIG. 3. The band unit comprises: a tapered press surface 5 which can be brought into tight contact with the back plate 3; an upper band 7 extending from a wide portion of the press surface 5 and having a slit 6 in the vicinity of a free end thereof; and a lower band 9 extending from a narrow portion of the press surface 5 and having a saw-toothed portion 8 in the vicinity of a free end thereof. The saw-toothed portion 8 of the free end of the lower band 9 is hooked into the slit 6 of the free end of the upper band 7, as shown in FIG. 2, thereby fastening the guide unit in the cavity 2. The band unit preferably comprises a soft material such as a soft plastic having a high tensile strength.

Figure 4:
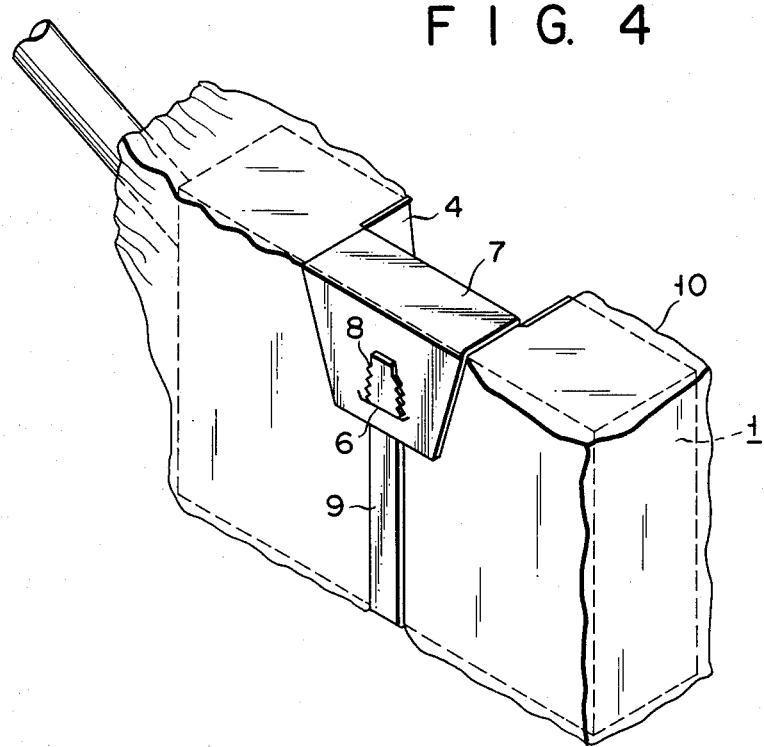
FIG. 4 shows the adaptor as viewed from the back.

When the adaptor having the structure described above is used, the probe 1 is first inserted in a plastic bag 10 (e.g., a thermoplastic resin bag such as a polyethylene film bag having a thickness of several tens of microns or less). The wedge-shaped cavity 2 of the probe 1 is tapered along the array of the elements 11 so as to become wider in the direction from an application surface which has the elements 11 thereon to an opposite surface thereto, as shown in FIG. 3. The guide unit shown in FIG. 1 is inserted in the cavity 2 through the bag 10. The press surface 5 of the band unit is then brought into tight contact with the back plate 3 of the guide unit. Thereafter, as shown in FIG. 4, the upper and lower bands 7 and 9 are wound to the back side of the probe, and the saw-toothed portion 8 of the lower band 9 is inserted in the slit 6 of the upper band 7, thereby fixing the bag 10 through the cavity 2. Therefore, the bag 10 is held by the guide unit in a shape substantially the same as that of the cavity 2 of the probe, so that the bag portion in the cavity 2 may not be loosened and wrinkles may not be formed in this bag portion. As a result, a sufficient space for cannulation is assured, and the probe 10 is completely separated from the cannula through the bag 10, thereby completely preventing contamination of the probe 1. For this reason, the probe 1 need not be disinfected or sterilized every time the probe 1 is used. Instead, the operator or doctor need only replace the bag 10 and the adaptor.

Figure 5:
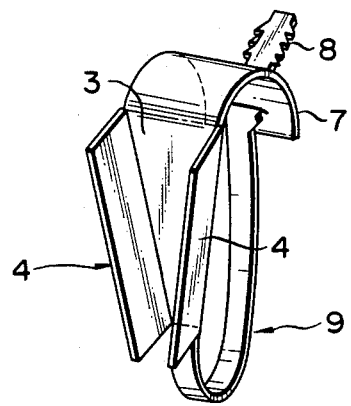
FIG. 5 is a perspective view of an adaptor according to a second embodiment of the present invention.

In the above embodiment, the guide unit is formed separately from the band unit. However, as in a second embodiment, the guide unit may be formed integrally with the band unit as shown in FIG. 5. In this case, the adaptor may be integrally molded by employing polypropylene. The rigidity of the guide unit and flexibility of the band unit may be controlled by adjusting the thickness of these units. The same reference numerals as used in FIGS. 1 and 2 denote the same parts in FIG. 5.

The adaptor of the present invention may also be effectively used while a cannula guiding block is mounted in the above-mentioned cavity.

Figure 6:
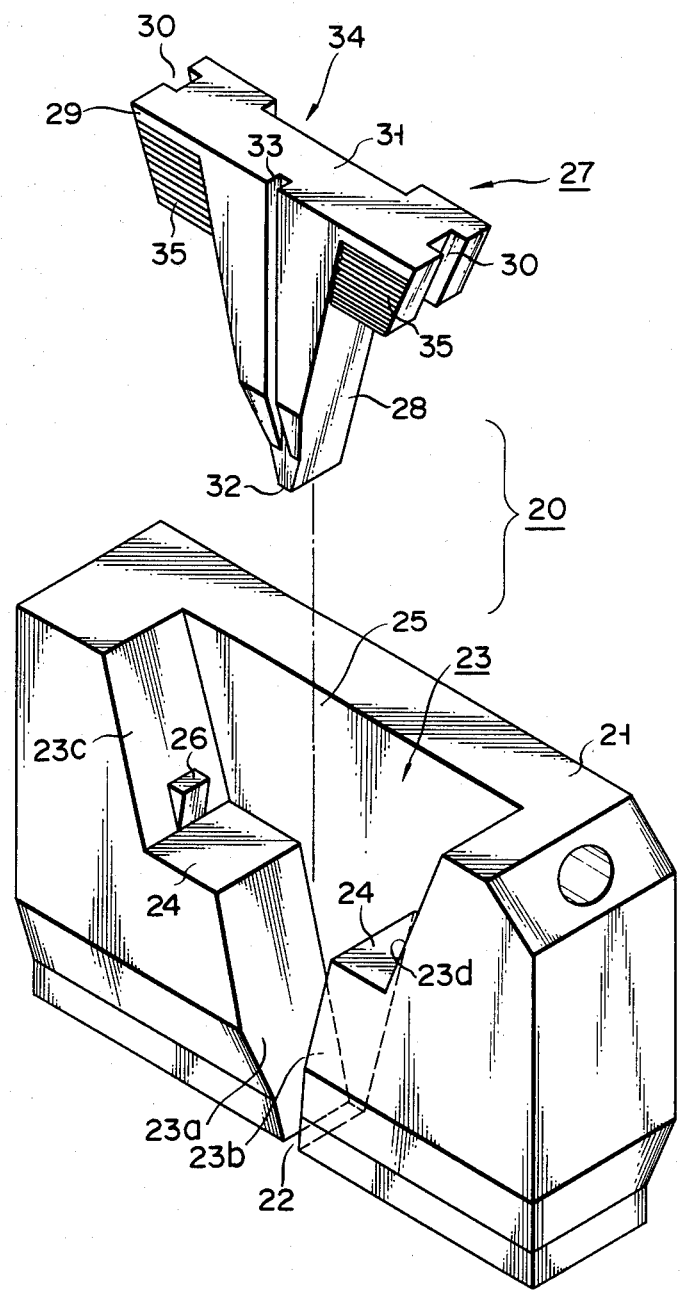
FIG. 6 is an exploded perspective view of a probe with which an adaptor of the present invention can be used.

FIG. 6 shows its application when a cannula guiding block is mounted in the cavity of the probe.

In FIG. 6, a transducer probe 20 comprises a carrier 21 having a plurality of ultrasonic transducer elements (not shown) arranged in at least one row on an application surface adapted to be located on the body surface of a patient (not shown), a slit 22 extending partly across the direction of the transducer elements arranged, a wedge-shaped cavity 23 defined by two pairs of the mutually facing tapered walls 23a, 23b, 23c and 23d, a pair of stepped portions 24, and a perpendicular V-shaped back wall 25 defined by the walls 23a to 23d and the stepped portions 24.

The carrier 21 further includes a pair of projections 26, as the stopper means to engage a guiding block 27 (described in detail later), formed on each of the mutually facing tapered walls 23c and 23d.

The external shape of the guiding block 27 is substantially complementary in shape to the wedge-shaped cavity 23 of the carrier 21, so as to fit therein.

The guiding block 27 comprises a narrow portion 28 to fit with the tapered walls 23a and 23b and a wide portion 29 to fit with the tapered walls 23c and 23d. Grooves 30 are formed along sides of the wide portion 29 to fit with the projections 26, respectively. A vertical cannula guide groove 33 is formed on one of the major surfaces to run from an upper surface 31 of the guiding block 27 to a distal end 32 of the narrow portion 28. The groove 33 has substantially the same width as that of the slit 22. A substantially V-shaped cannula guide groove 34 is formed in the other of the major surfaces and is gradually tapered from the upper surface 31 to the distal portion 32.

Corrugated surfaces 35 are formed on both major surfaces of the wide portion 29 to allow easy attachment of the guiding block 27 to or detachment from the carrier 21.

The guiding block 27 is fitted in the cavity 23 such that either the cannula guide groove 33 or the cannula guide groove 34 faces outward from the carrier 21.

Figure 7:
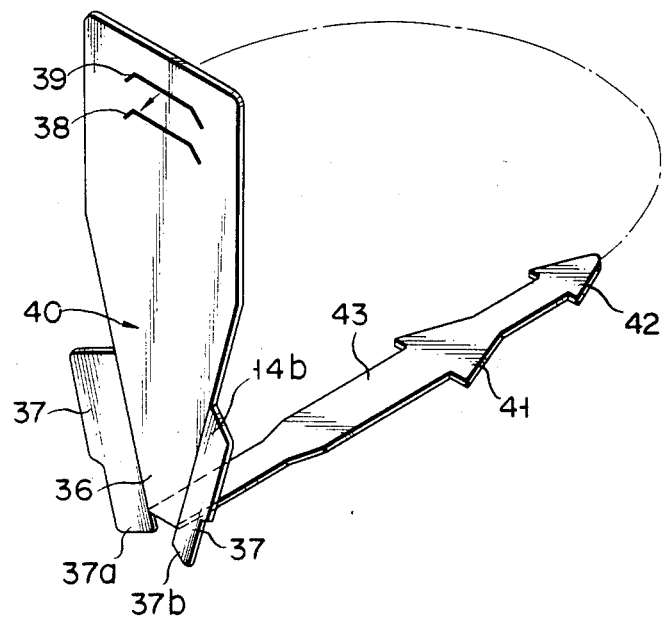
FIG. 7 is a perspective view of an adaptor according to a third embodiment of the present invention which is used with the probe (FIG. 6)

When the adaptor of the present invention is used for the probe having the structure described above, the operator first inserts the carrier 21 in a bag in the same manner as described with reference to FIG. 3. The adaptor is then fitted in the cavity 23. Thereafter, the guiding block 27 is mounted in the adaptor. The adaptor used with this carrier 21 is illustrated in FIG. 7. Referring to FIG. 7, the adaptor comprises: a substantially V-shaped back plate 36 complementary to a shape defined by the tapered walls 23a and 23b of the cavity 23; a pair of side plates 37 which are integrally formed with the back plate 36 along two sides thereof and each of which has a width substantially equal to that of each of the tapered walls 23a and 23b; an upper band 40 extending from the upper end of the back plate 36 and having a pair of slits 38 and 39 spaced apart from each other; and a lower band 43 extending from the lower end of the back plate 36 and having hooks 41 and 42 spaced apart from each other.

Each of the lower ends 37a and 37b of the side plates 37 is preferably extended lower than the lower end of the back plate 36 by about 1 mm, as shown in FIG. 7. This prevents the presence of a loosened portion of the bag in the slit 22, thereby effectively preventing contamination of the probe caused by blood or the like.

The side plates 37 described above can be formed by partially cutting (not shown) connecting portions between the lower band 43 and the respective side plates 37.

A projection of about 1 mm may also be formed at the lower end of the back plate in the embodiments shown in FIGS. 1 and 5.

Figure 8:
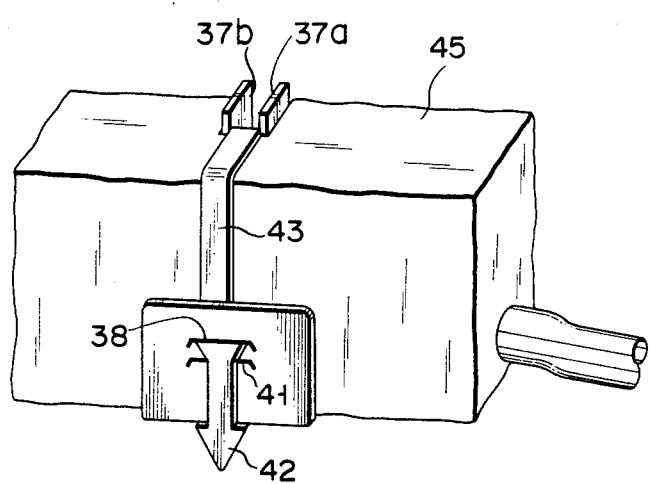
FIG. 8 is a perspective view showing the adaptor (FIG. 7) mounted on the probe (FIG. 6).

FIG. 8 shows the adaptor (FIG. 7) connected to the probe (FIG. 6) by a bag 45. The upper and lower bands 40 and 43 engage with each other through the slit 38 and the hook 41. The lower ends 37a and 37b of the side plates 37 slightly extend upward from the bag 45.

In the above embodiments, the upper band and the lower band engage with each other through a stopper means comprising a combination of a slit at one free end and a hook or saw-toothed portion at the other free end. However, any other stopper means may be adopted. Furthermore, the band unit may comprise an elastic material such as rubber. In this case, stopper means are mounted at two ends of the band unit to engage the upper band with the lower band.

According to the present invention, the probe is first covered with the bag. The bag is then held in place by utilizing the cannula guide cavity of the probe, thereby preventing contamination of the probe which is caused by blood at the time of cannulation, without impairing the probe functions. As a result, the conventional disinfection and sterilization procedures of the probe for each patient can be substantially eliminated.

What is claimed is:

1. An adaptor for a cannula guide type ultrasonic transducer probe which guides a cannula along a cavity of the ultrasonic transducer probe and which holds a bag covering said probe in position, said cavity being formed in one major surface of said probe and being tapered along an array of ultrasonic transducer elements so as to become wider in a direction from an application surface which has the ultrasonic transducer elements thereon to an opposite surface thereto, comprising: a guide unit having a substantially trapezoidal back plate whose unequal sides define upper and lower ends of the back plate and a pair of side plates, said back plate having a shape complementary to the shape of a back wall of said cavity and adapted to be fitted in said cavity while said bag covers said probe to thereby allow cannula access alongside said bag when said cannula is disposed in said guide unit, and said pair of side plates being integrally formed with said back plate along two sides thereof; and a band unit mounted such that upper and lower free ends thereof respectively extend from upper and lower ends of said back plate, said upper and lower free ends of said band unit having engaging means for securing said adaptor to said probe.

2. An adaptor according to claim 1, wherein said guide unit is formed separately from said band unit.

3. An adaptor according to claim 1, wherein said guide unit is formed integrally with said band unit.

4. An adaptor according to claim 1, wherein each of said side plates has a lower end which is lower than the lower end of said back plate by 1 mm.

5. An adaptor according to claim 1, wherein said guide unit comprises a rigid material, and said band unit comprises a soft material.

6. An adaptor according to claim 1, wherein said bag comprises a flexible, thermoplastic resin bag having a thickness of not more than several tens of microns.

7. An adaptor according to claim 1, wherein said stopper means comprises a combination of a slit and a hook.

8. An adaptor for an ultrasonic transducer probe which holds a bag in position and guides a cannula along the ultrasonic transducer probe having a carrier, said adaptor including a guiding block, said carrier having a cavity defined by a pair of tapering narrow portion side walls and a pair of tapering wide portion side walls, said pair of tapering narrow portion side walls being tapered so as to become further apart in a direction away from an application surface which has ultrasonic transducer elements thereon to an opposite surface thereto, and said pair of tapering wide portion side walls being further tapered next to said tapering narrow portion side walls through stepped portions, and said guiding block having an external shape so as to fit in said cavity and having a cannula guide groove which is formed on at least one major surface of said guiding block so as to extend from an upper surface to a distal end thereof, said guide block having a substantially trapezoidal back plate and a pair of side plates, said back plate having a shape complementary to a portion of a cavity back wall which is defined by said tapering narrow portion side walls, said back plate being fitted in said cavity while said bag covers said probe to thereby allow cannula access alongside said bag when said cannula is disposed in said guide unit, and said pair of side plates being formed integrally with said back plate along two sides thereof; and a band unit extending upward and downward from upper and lower ends of said back plate and having upper and lower free ends which have engaging means for securing said adaptor to said probe.

9. An adaptor according to claim 8, wherein each of said pair of side plates has a lower end lower than the lower end of said back plate by 1 mm.

* * * * *